United States Patent
Kim et al.

(10) Patent No.: US 8,859,783 B2
(45) Date of Patent: Oct. 14, 2014

(54) INDIRUBIN-3'-OXIME DERIVATIVES AS POTENT CYCLIN DEPENDENT KINASE INHIBITORS

(75) Inventors: Yong-Chul Kim, Gwangju (KR); Jae-Il Kim, Gwangju (KR); Soo-Ho Ban, Gwangju (KR); Soon-Young Jeong, Gwangju (KR); Soo-Jeong Choi, Gyeongsangnam-do (KR); Jung-Eun Lee, Seoul (KR)

(73) Assignee: Anygen Co., Ltd., Jeollanam-Do (KR)

( * ) Notice: Subject to any disclaimer, the term of this patent is extended or adjusted under 35 U.S.C. 154(b) by 9 days.

(21) Appl. No.: 13/576,105

(22) PCT Filed: Jan. 28, 2011

(86) PCT No.: PCT/KR2011/000611
§ 371 (c)(1),
(2), (4) Date: Jul. 30, 2012

(87) PCT Pub. No.: WO2011/096676
PCT Pub. Date: Aug. 11, 2011

(65) Prior Publication Data
US 2012/0295948 A1  Nov. 22, 2012

(30) Foreign Application Priority Data
Feb. 5, 2010 (KR) .................. 10-2010-0010715

(51) Int. Cl.
C07D 209/38 (2006.01)
A61K 31/404 (2006.01)
C07D 403/04 (2006.01)

(52) U.S. Cl.
CPC ............ *A61K 31/404* (2013.01); *C07D 403/04* (2013.01)
USPC ........................................................ 548/457

(58) Field of Classification Search
None
See application file for complete search history.

(56) References Cited

U.S. PATENT DOCUMENTS

2010/0167300 A1* 7/2010 Esmaeli-Azad ................. 435/6

OTHER PUBLICATIONS

Kim et al, Atherosclerosis (2010) 211(1), 77-83.*
Choi et al. J. Med. Chem. (2010), 53(9), 3696-3706.*
Choi et al. Bioorg. Med. Chem. Lett. 20(2010), 2033-2037.*
Beauchard et al. Bioorg. Med. Chem. (2009), 17(17), 6257-6263.*
Beauchard et al. Bioorg. Med. Chem. (2006), 14(18), 6434-6443.*
Kim et al. Bioorg. Archives of Pharmacal Research (2009), 32(6), 915-922.*
Park et al. Bioorg. Med. Chem. Lett. (2009), 19(8), 2282-2284.*
Zhang et al. European J. Med. Chem. 41 (2006) 373-378.*

* cited by examiner

*Primary Examiner* — Nyeemah A Grazier
(74) *Attorney, Agent, or Firm* — Kenyon & Kenyon LLP

(57) ABSTRACT

The present invention relates to an indirubin-3'-oxime derivative as potent cyclin dependent kinase inhibitor with anti-cancer activity. More particularly, this invention relates to an indirubin-3'-oxime derivative as potent cyclin dependent kinase inhibitor having excellent anti-cancer activity against human lung cancer cell, human fibro sarcoma cell, human colon cancer cell, human leukemia cell, human stomach cancer cell, human nasopharyngeal cancer cell and/or human breast cancer cell.

1 Claim, 5 Drawing Sheets

1
5-nitroindirubin-3'-oxime 2
5'-bromo-5-nitro-indirubin-3'-oxime 11b ( $R_1$=OH, $R_2$=$NO_2$)
5'-hydroxy-5-nitro-indirubin-3'-oxime

A

B

C

D

INDIRUBIN-3'-OXIME DERIVATIVES AS POTENT CYCLIN DEPENDENT KINASE INHIBITORS

This is a 371 national phase application of PCT/KR2011/000611 filed 28 Jan. 2011, claiming priority to Korean Patent Application No. 10-2010-0010715 filed 5 Feb. 2010, the contents of which are incorporated herein by reference.

TECHNICAL FIELD

The present invention relates to an indirubin-3'-oxime derivative as potent cyclin dependent kinase inhibitor with anti-cancer activity. More particularly, this invention relates to an indirubin-3'-oxime derivative as potent cyclin dependent kinase inhibitor having excellent anti-cancer activity against human lung cancer cell, human fibro sarcoma cell, human colon cancer cell, human leukemia cell, human stomach cancer cell, human nasopharyngeal cancer cell and/or human breast cancer cell.

BACKGROUND ART

Cyclin-dependent kinases (CDKs), belong to a group of serine/threonine kinases involved in the regulation of cell cycle progression, neuronal function, differentiation and apoptosis. Their activity is tightly regulated by multiple mechanisms including binding to corresponding cyclins, of which level of expression oscillates throughout the different phases of the cell cycle. Different CDK/cyclin complexes are activated during each cell cycle step through G1, S, G2, M phases. Sequential phosphorylation of the retinoblastoma protein (pRb) by CDK4/cyclin D, CDK6/cyclin D in early G1 phase and CDK2/cyclin E in late G1 phase causes the release of the E2F, proteins of transcription factor. In turn, E2F proteins lead to transcriptional activation of a set of genes required for entry into S-phase of the cell cycle. CDK2 is subsequently activated by cyclin A during the late stages of DNA replication, S-phase, and promotes appropriately timed deactivation of E2F to prevent apoptosis triggered by persistent E2F activity. Finally, CDK1 in complex with cyclin A or B is thought to be have roles in regulating the G2/M checkpoint and driving cells through mitosis.

In addition to the cell cycle control, other roles have been determined for CDK2, 7, 8 and 9. For example, CDK2/Cyclin E is important to the p53 mediated DNA damage response pathway and CDK7, 8 and 9 are involved in the regulation of transcription initiation and elongation through phosphorylation of RNA polymerase. Therefore, CDKs affect cell growth and survival through several different mechanisms and proper regulation of CDK activity is important to various cellular processes. It is now recognized that deregulation of CDKs by abnormal high expression of cyclin such as cyclin D and cyclin E or mutation occurs in many human tumors. For example, the expression and catalytic activity of CDK2/cyclin E complexes is increased in colorectal, ovarian, breast, and prostate cancers and elevated expression of cyclin E in primary tumors has correlation with poor survival rates for breast cancer patients. Abnormal expression of CDK1/cyclin B complexes has been also observed in some cases, prostate adenocarcinoma and lung cancer.

Although a report have shown that CDK2 may not be required for cell cycle progression and proliferation, recent reports suggested that melanocytes and hepatocytes may be dependent on CDK2 for proliferation and survival. Also, an investigation of simultaneous depletion of CDK1 and CDK2 was reported to provide increased efficacy in anti-proliferation of tumor cell lines, compared with targeting either CDK1 or CDK2 alone. In addition, emerging evidences indicate that certain tumor cells may require specific interphase CDKs for proliferation. Thus inhibition of CDKs may provide an effective strategy to control tumor growth as attractive targets for cancer therapy.

To date, a number of small-molecule CDK inhibitors are currently under clinical trials. These inhibitors are flat, small heterocycles which act by competition with ATP in the kinase ATP-binding site. Among them, flavopyridol, was the first CDK inhibitor to enter clinical evaluations. R-Roscovitine (trisubstituted purine analog) and BMS-387032 (aminothiazole) are selective for CDK2/cyclin E and PD-0332991 (pyridopyrimidine) is highly selective for CDK4/cyclin D and CDK6/cyclin D. Indirubin, a bis-indole scaffold and its derivatives have been investigated with considerable interests as potent inhibitors targeting important protein kinases such as CDK, GSK-3β, and aurora kinases.

In WO 2005/070416 A1, the inventors of present application has disclosed 'indirubin derivatives having anticancer property against human cancer cell line'. In this disclosure, indirubin derivative having anticancer property by inhibiting cell proliferation as to human cancer cell line has been disclosed. Among disclosed indirubin derivatives, 5'-bromo-5-nitro-indirubin-3'-oxime showed the most potent anti-proliferative effects (IC50=0.79~2.9 μM) against various cancer cell lines. However, the further substitution of radicals at the 5' position in indirubin skeleton has not been made as well as anti-cancer activity regarding these compounds has not been measured. Further, there has been no report regarding the synthesis and biological evaluations exploring the effect of various substitutions at the 5' position of indirubin skeleton.

On the other hand, the inventors of present application have found that the additional substitution at the 5' position is clearly favorable compared with 5-nitro-indirubin-3'-oxime analog. Therefore, the inventors of present application have completed the invention by design, synthesis and biological evaluation including CDK inhibitory activity, anti-proliferative activity and in-vivo anti-cancer activity of novel 5',5-substituted indirubin-3'-oxime analogs.

DISCLOSURE OF INVENTION

Solution to Problem

The object of present invention is to provide an indirubin-3'-oxime derivative compound as cyclin dependent kinase inhibitor with anti-cancer activity represented by formula (I)

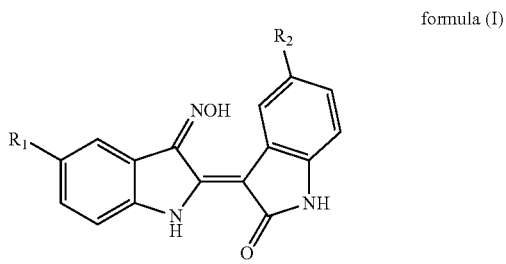

formula (I)

wherein
$R_1$ is selected from F, Cl, OH or $CH_3$
$R_2$ is selected from F, Cl or $NO_2$ Further, the present invention provide a compound wherein it comprises that $R_1$ is OH and $R_2$ is $NO_2$; a compound wherein it comprises that $R_1$ is F and $R_2$ is $NO_2$.

Further, the present invention provide i) a compound wherein it comprises that $R_1$ is OH and $R_2$ is Cl, ii) a compound wherein it comprises that $R_1$ is OH and $R_2$ is F, iii) a compound wherein it comprises that $R_1$ is Cl and $R_2$ is $NO_2$, and iv) a compound wherein it comprises that $R_1$ is $CH_3$ and $R_2$ is $NO_2$.

Further, the present invention provide an indirubin-3'-oxime derivative compound represented by formula (I) having excellent anti-cancer activity against human lung cancer cell line, human fibro sarcoma cell line, human colon cancer cell line, human leukemia cell line, human stomach cancer cell line, human nasopharyngeal cancer cell line and/or human breast cancer cell line.

The further object of present invention is to provide an anti-cancer composition comprising said indirubin-3'-oxime derivative compound and pharmaceutically acceptable carrier.

BRIEF DESCRIPTION OF DRAWINGS

FIG. 2(a) shows a network of hydrogen bonds (green dashed lines) between 2 and the kinase backbone. Binding mode of 2 with CDK2 display three hydrogen bonds with the CDK2 hinge region, additional hydrogen bond between the oxime moiety and carbonyl oxygen of Gln131. And also, 5-nitro group forms salt bridge with the side chains of Lys33, Asp145. FIG. 2(b) shows a van der Waals surface of CDK2 with 2 in CPK representation. 5'-Bromo group is projected toward the outer aqueous space of ATP binding pocket that present the positively charged amino acid residue, Lsy89. FIG. 2(c) shows a network of hydrogen bonds (green dashed lines) between 11b and the kinase backbone. 11b forms an additional hydrogen bond between the 5'-hydroxy group and the carboxylic acid of Asp86. This may further improve CDK2 inhibitory activity. FIG. 2(d) shows a molecular surface representation of CDK2 with 11b bound in the ATP binding site. Some important amino acids lying within binding surface are displayed. The 5'-hydroxy group is pointing out of the pocket toward solvent.

FIG. 5(a) shows that the SD-Rats were injected with RK3E-ras-Luc cells ($5 \times 10^6$/100 μl). When the tumor reached 5 mm in size, the rats were injected intravenously with 11b (5 mg/kg) in non-anesthesia states every other day for a total five times. The tumor size was measured by caliper as described in specification. FIG. 5(b) shows a representative excised subcutaneous tumor from the control and 11b treated rats. FIG. 5(c) shows an in vivo bioluminescence imaging assay from the control and 11b treated rats.

FIG. 6(a) shows H&E staining of tumor sections (left), TUNEL assay on paraffin sections from solid tumor (middle), and immunohistochemical staining for PCNA (right), FIG. 6(b) shows positive cells for TUNEL assay, FIG. 6(c) shows positive cells for PCNA immunostaining. Cells were counted in triplicate. Columns, mean; bars, SD.

MODE FOR THE INVENTION

Figure 1:
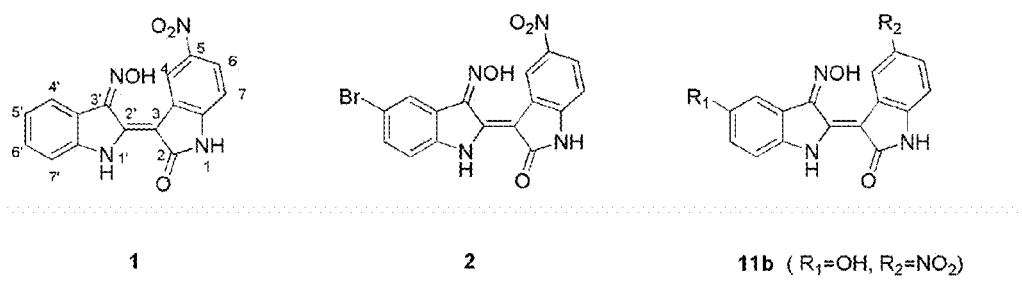
FIG. 1 shows a structure of indirubin derivatives related to present invention.

A new series of indirubin-3'-oxime derivatives with combined substitutions at 5' and 5 positions was designed and synthesized to improve the inhibitory potencies against CDK2/cyclin E, a target of anti-cancer agents including indirubin derivatives. The binding mode of 5'-substituted analogs with OH or halogens were predicted with a molecular docking study in the ATP binding site of CDK2, showing the critical interactions that might explain the improved CDK2 inhibitory activity.

Structure-activity relationship analysis showed that OH and halogen groups were preferred to the electron donating groups such as $CH_3$ and $OCH_3$ at 5' position. Among the synthesized derivatives, 5'-hydroxy-5-nitro-indirubin-3'-oxime (11b) and 5'-fluoro-5-nitro-indirubin-3'-oxime (13b) displayed potent inhibitory activities against CDK2 with IC50 values of 1.9, 1.7 nM, respectively and anti-proliferative effects against several human cancer cell lines with IC50 values in the range of 0.2~3.3 μM. A study of kinase selectivity profile of 11b at 10 different receptor tyrosine kinase and serine/threonine kinase panel resulted in more than 500-fold selectivity for the inhibitory activity against CDK. The anti-cancer activity of 11b was further confirmed in-vivo xenograft animal model with i.v. administration of 5 mg/kg dose, showing 84% reduction of the tumor volume without loss of body weight compared with control animals. The mechanism of anti-tumor activity through the histological analysis was shown by the markers for apoptosis and proliferation, which were increased and decreased, respectively.

Further, other analogs, such as, 5'-hydroxy-5-chloro-indirubin-3'-oxime (11a), 5'-hydroxy-5-fluoro-indirubin-3'-oxime (11c), 5'-chloro-5-nitro-indirubin-3'-oxime (12b) and 5'-methyl-5-nitro-indirubin-3'-oxime (14b) can be considered as effective anti-cancer agent.

The present invention can be explained more concretely as follows.

Molecular Docking for Designing Strategy

Figure 2:
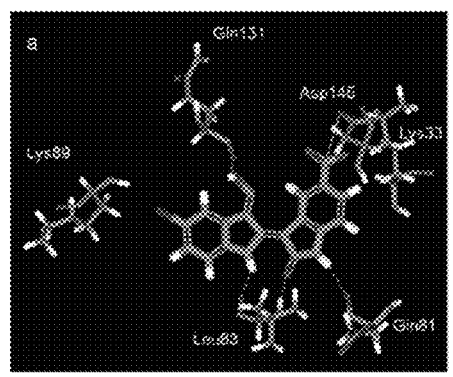
FIG. 2 shows a binding mode of 2 and 11b to the ATP binding site of CDK2.
Figure 2:
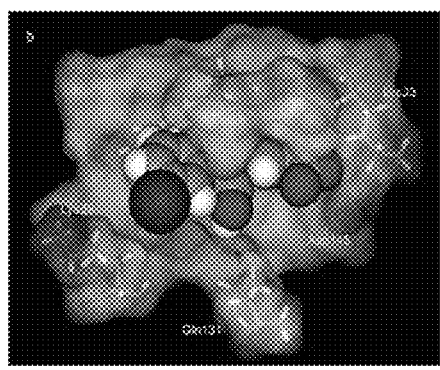
Figure 2:
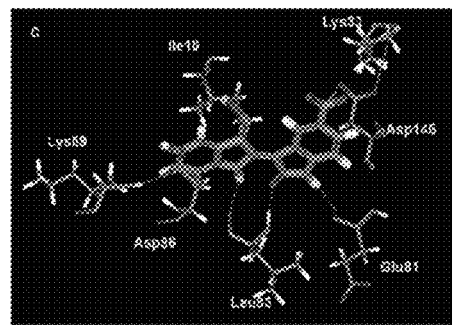
Figure 2:
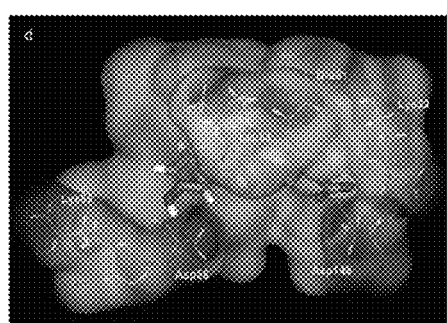

To address the enhanced anti-proliferative effect of compound 2, a molecular docking study was carried out in the ATP binding site of CDK2 (FIG. 2) using CDocker, a CHARMm-based molecular dynamics docking program (Discovery Studio 2.0). FIG. 2(a) shows that the nitrogen at position 1', the carbonyl oxygen at position 2, and the nitrogen at position 1 of compound 2 maintain three hydrogen bonding interactions with the hinge segments (Gln81, Leu83) of ATP binding site. In addition, 3'-hydroxyl group of oxime moiety forms a hydrogen bonding with backbone carbonyl of Gln131 and 5-nitro group contributes to a salt bridge with the side chains of Lys33, Asp145. FIG. 2(b) depicts the binding surface with electrostatic potential within 4 Å around the ligand, 2 and 5'-Br group might be projected toward the outer aqueous space of ATP binding pocket where a positively charged amino acid residue, Lys89 is located as a virtual binding partner. It could be hypothesized that an additional electrostatic interaction of the lone pair electrons of 5'-Br group with the positively charged Lys89 residue might provide higher binding affinity with CDK2 and consequently contribute to the more potent anti-proliferative activity of 2, compared with a 5'-unsubstituted-indirubin-3'-oxime analog, 1. According to the data obtained by docking study, derivatization at 5'-position along with 5-substituents (Cl, NO$_2$, F, and OCF$_3$) may be ideal for the strategy of modifications on the indirubin scaffold to optimize the binding affinity for CDK2.

To investigate the structure-activity relationships at the 5' position of indirubin skeleton for CDK inhibitory and anti-proliferative activities, following groups were selected for the derivatizations 1) 5'-F, 5'-Cl, which can form similar electrostatic interaction with Lys89 as in the case of 5'-bromo analog, 2 2) 5'-OH to provide additional hydrogen bond with CDK2 and introduce hydrophilic character 3) 5'-OCH$_3$, 5'-CH$_3$, expecting contrast effects compared with halogen substituted analogs.

In fact, a docking model of a representative designed molecule, 5'-hydroxy-5-nitro-indirubin-3'-oxime derivative (11b) in the ATP binding site in CDK2 showed that new hydrogen bonding interaction might be formed between 5'-OH group of 11b and Asp86 in the solvent accessible region and the oxime moiety of 11b interacted with Ile10 instead of Gln131. FIG. 2(d) exhibited a binding surface with electrostatic potential within 4 Å around 11b, indicating how the 5'-OH protrude into the outer aqueous surface, solvent accessible region.

Chemistry

For the synthesis of 5',5-substituted-3'-indirubin oxime derivatives, 5-substituted indoxyl N,O-diacetate 5a-d were prepared starting from corresponding 5-substituted anthranilic acids 3a-d (Scheme 1).

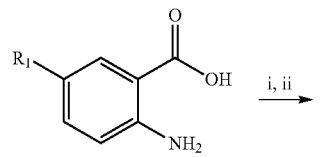

3a: R$_1$ = OH
3b: R$_1$ = Cl
3c: R$_1$ = F
3d: R$_1$ = CH$_3$

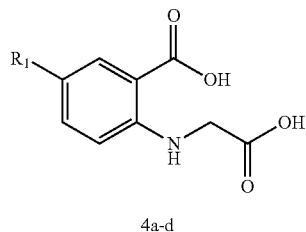

4a-d

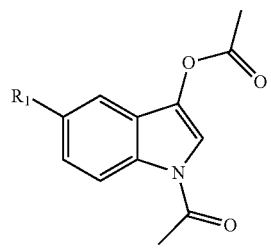

5a: R$_1$ = O-acetyl
5b: R$_1$ = Cl
5c: R$_1$ = F
5d: R$_1$ = CH$_3$

Briefly, compounds 3a-d were subjected to the conditions of reductive alkylation with ethylglyoxalate, and subsequent hydrolysis to yield dicarboxylic acids, 4a-d, which were finally cyclized in acetic anhydride to afford 5a-d. In the case of 5-hydroxy analog, the cyclized compound 5a was obtained as a tri-acetate form since the phenolic hydroxyl group was also acetylated under the condition of cyclization.

In Moon, M. J. et al., Bioorg. Med. Chem. 2006, 14, 237-246, 5',5-substituted-3'-indirubin oxime derivatives, 11-14 were synthesized from the conjugate reaction of 5-substituted indoxyl N, O-diacetate 5a-d with various 5-substituted isatin analogs, 6a-d to yield 5',5-substituted indirubin derivatives, 7-10 under basic condition followed by the reaction of each indirubins 7-10 with hydroxylamine for the conversion of ketone into 3'-oxime groups (Scheme 2).

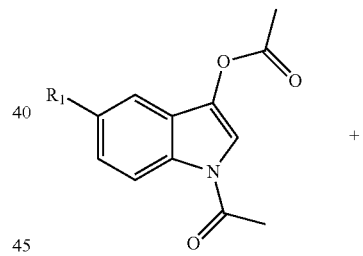

5a: R$_1$ = O-acetyl
5b: R$_1$ = Cl
5c: R$_1$ = F
5d: R$_1$ = CH$_3$

+

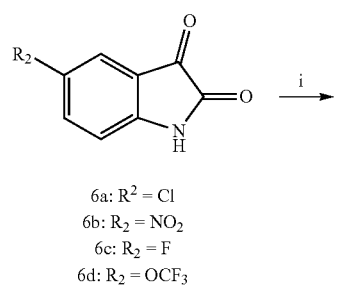

6a: R$^2$ = Cl
6b: R$_2$ = NO$_2$
6c: R$_2$ = F
6d: R$_2$ = OCF$_3$

-continued

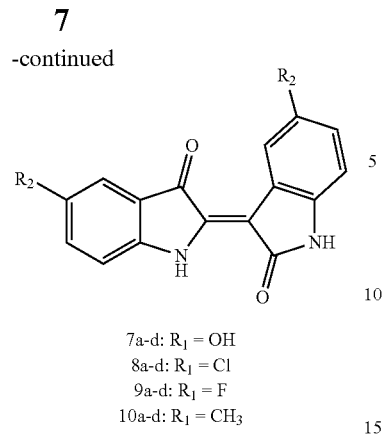

7a-d: R₁ = OH
8a-d: R₁ = Cl
9a-d: R₁ = F
10a-d: R₁ = CH₃
R₂ = Cl, NO₂, F, OCF₃ ii ↓

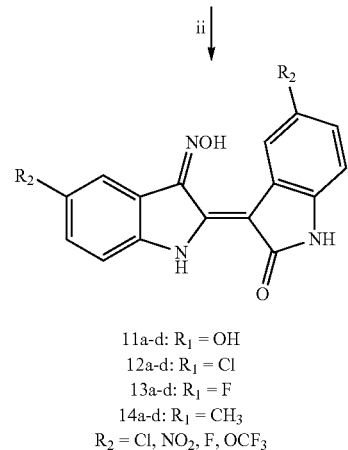

11a-d: R₁ = OH
12a-d: R₁ = Cl
13a-d: R₁ = F
14a-d: R₁ = CH₃
R₂ = Cl, NO₂, F, OCF₃

5'-Methoxy-5-substituted-3'-oxime compounds, 16a-c were synthesized from corresponding 5'-hydroxy-5-substituted indirubin derivatives, 15a-c by methylation of the phenolic hydroxyl groups and subsequent reaction with hydroxylamine (Scheme 3).

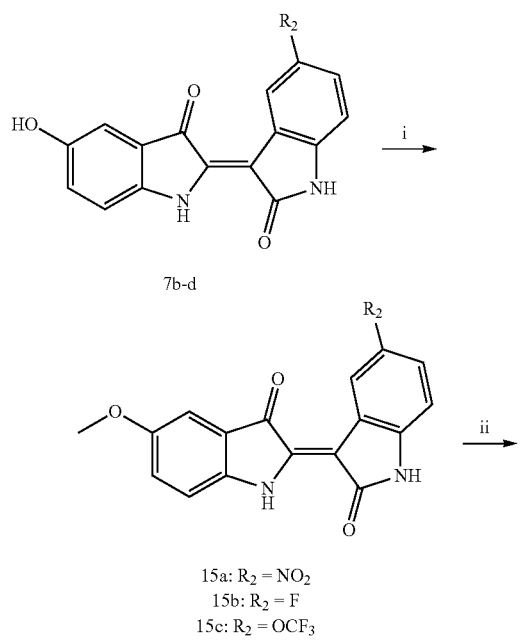

15a: R₂ = NO₂
15b: R₂ = F
15c: R₂ = OCF₃

-continued

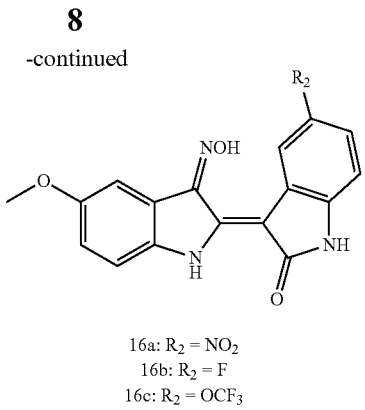

16a: R₂ = NO₂
16b: R₂ = F
16c: R₂ = OCF₃

CDK Inhibitory Activity and Kinase Selectivity Profile

Figure 3:
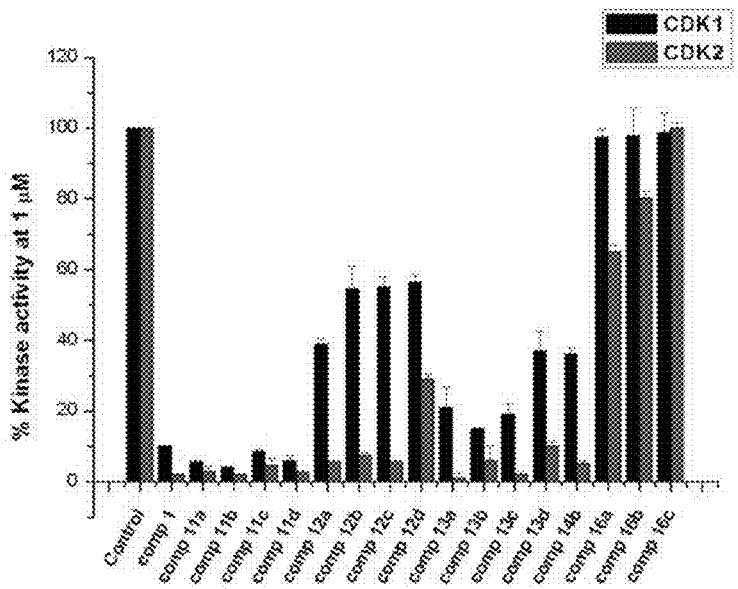
FIG. 3 shows a percentage of CDK1, CDK2 activity at 1 μM of 5',5-substituted indirubin-3'-oxime derivatives. A series of indirubin derivatives are tested at 1 μM for their effects on CDK1/cyclin B, CDK2/cyclin E, as described in specification. Experiment has been also performed with 5-nitroindirubin-3'-oxime (1) for comparison.

5',5-substituted-indirubin-3'-oxime derivatives were initially evaluated for their inhibitory activities against CDK1/cyclinB, CDK2/cyclinE in 1 μM (FIG. 3). 5-nitroindirubin-3'-oxime, 1 was tested together for the comparison of the effects of substitutions at the 5'-position. The inhibitory activity and selectivity of the compounds for CDK2 over CDK1 were turned out to be dependent on the 5'-substitutents at $R_1$-position. In general, 5',5-substituted indirubin-3'-oxime derivatives presented potent inhibitory activities against CDK2 with more than 90% inhibitory potency in 1 μM, except for 12d, 16a-c. Especially, 5'-OH analogs, 11a-d showed the highest inhibitory potency against both of CDK1 and CDK2. Although the 5'-OH at $R_1$ position resulted in decreased CDK2 selectivity over CDK1, this result may be important in the view of the concept that simultaneous inhibitor against CDK1 and CDK2 may have additional benefits in terms of anticancer activity, according to group the literatures. Moreover, substitution of 5'-hydroxyl group improved the water solubility, which has been a major drawback among the physicochemical properties of indirubin analogs. In contrast to 5'-OH-substituted indirubin-3'-oxime derivatives, 5'-chloro and 5'-fluoro substituted indirubin-3'-oxime derivatives, 12a-d and 13a-d, maintained potent CDK2 inhibitory activity with 6-10 fold selectivity over CDK1. For example, 5'-chloro-5-nitro-indirubin-3'-oxime, 12b was about 8 fold more potent against CDK2 than CDK1 (Table 1).

TABLE 1

CDK2/cyclin E inhibitory activities of 5',5-substitutied indirubin-3'-oxime derivatives

| Compound | $R_1$ | $R_2$ | $IC_{50}$ (nM)[a] |
|---|---|---|---|
| 11a | OH | Cl | 5.27 |
| 11b | OH | NO₂ | 1.91[b] |
| 11c | OH | F | 2.25 |
| 11d | OH | OCF₃ | 8.32 |
| 12a | Cl | Cl | 11.1 |
| 12b | Cl | NO₂ | 23.5[b] |
| 12c | Cl | F | 10.1 |
| 12d | Cl | OCF₃ | 76.2 |

TABLE 1-continued

CDK2/cyclin E inhibitory activities of 5',5-substitutied indirubin-3'-oxime derivatives

| Compound | $R_1$ | $R_2$ | $IC_{50}$ (nM)[a] |
|---|---|---|---|
| 13a | F | Cl | 8.01 |
| 13b | F | $NO_2$ | 1.71 |
| 13c | F | F | 1.83 |
| 13d | F | $OCF_3$ | 60.3 |
| 14b | $CH_3$ | $NO_2$ | 8.68 |
| 16a | $OCH_3$ | $NO_2$ | 2,950 |
| 16b | $OCH_3$ | F | 4,120 |
| 16c | $OCH_3$ | $OCF_3$ | 8,620 |
| 1 | H | $NO_2$ | 7.35 |

A series of indirubin derivatives were tested at ten concentrations in CDK2/cyclin E kinase assay, as described in the Experimental Section. $IC_{50}$ values were calculated from the dose response curves. $IC_{50}$ values of 11b and 12b in CDK1/cycline B kinase assay are 13 nM and 195 nM, respectively.

The decreased potency of CDK1 inhibition by 5'-halogenations could be further supported by a report of 5'-bromo-5-nitro-indirubin-3'-oxime, 2, which showed decreased CDK1 inhibitory activity ($IC_{50}$=190 nM) compared with 5-nitro-indirubin-3'-oxime, 1. Among the series of compounds with electron donating groups at 5' position, 14b with 5'-$CH_3$ maintained potent CDK2 inhibitory activity with selectivity over CDK1 by 7-fold. However, 5'-$OCH_3$ substituted derivatives (16a-c) displayed weak or no inhibitory activity against CDK1 and CDK2 in 1 μM.

The structure-activity relationships of 5',5-indirubin-3'-oxime derivatives for their CDK2 inhibitory activities were analyzed with $IC_{50}$ values. (Table 1) Most of the derivatives showed potent inhibitory activities with $IC_{50}$ values of 1~70 nM, except for 5'-$OCH_3$ derivatives, 16a-c. Regarding the effects of 5'-substituents at $R_1$ position, the CDK2 inhibitory activities were increased by following order —$OCH_3$<—Cl<—H, —$CH_3$<—OH, —F. For example, 5'-chloro-substituted-indirubin-3'-oxime compounds 12a-d showed 10-fold reduced CDK2 inhibitory activity ($IC_{50}$=10~76 nM) than 5'-fluoro-indirubin-3'-oxime derivatives, 13a-c ($IC_{50}$=1~8 nM). An electron-donating group, 5'-$OCH_3$ ?substituent (16a-c) displayed dramatically reduced CDK2 inhibitory activity with $IC_{50}$ values of 2-8 μM, although another electron-donating group, 5'-$CH_3$-substituted indirubin-3'-oxime, 14b showed 270 fold enhanced inhibitory effect compared with 16b. Particularly, the most potent CDK2 inhibitors 11b, 13b and 13c showed approximately 2 nM of $IC_{50}$ values against CDK2 with approximately 4 fold higher potency than 5'-unsubstituted-5-nitro-indirubin-3'-oxime, 1 ($IC_{50}$=7 nM). In the analysis of the effect of 5-substitutions at $R_2$ position of indirubin-3'-oxime derivatives, nitro and fluoro groups were generally more favorable for CDK2 inhibition rather than other 5-substituents, such as chloro or trifluoromethoxy groups. Taken together, indirubin-3'-oxime analogs with combination of substituents providing electronic effects such as OH and F at 5'-position and $NO_2$ and F at 5-position displayed potent inhibitory activity against CDK2.

Figure 4:
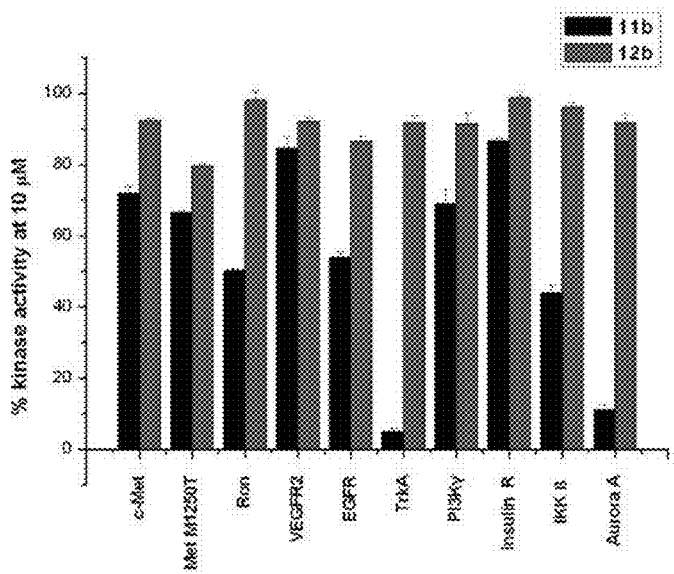
FIG. 4 shows a kinase panel screening of 11b, 12b at 10 μM. Compounds 11b, 12b are tested at 10 μM concentration against more diverse panel of kinases comprising of receptor tyrosine kinases and serine/threonine kinases, as described in specification. 1 μM 11b shows 9% inhibitory activity against TrkA and $IC_{50}$ values of 11b against two serine/threonine kinases, Aurora A (1 μM) and IKKβ (10 μM), and a receptor tyrosine kinase, TrkA (4 μM) are calculated from the dose response curves.

The representative potent and selective CDK2 inhibitors, 11b and 12b were further evaluated against more diverse panel of kinases comprising of receptor tyrosine kinases and serine/threonine kinases (FIG. 4). 11b showed weak inhibitory activity only against Aurora A, IKKβ and TrkA among the tested kinases, and the $IC_{50}$ values were in the range of 1~10 μM. 12b displayed negligible inhibitory activities against all the tested kinase panel. Since the $IC_{50}$ values of 11b and 12b against CDK1 and 2 are in the low nanomolar ranges, the kinase selectivity profile among the serine/threonine kinases and receptor tyrosine kinases tested in this study could be significantly favorable for CDK1 and CDK2.

Anti-Proliferative Activity

The anti-proliferative activities of 5',5-substituted indirubin-3'-oxime derivatives against several cancer cell lines, A549, HT1080, HCT116, K562, SNU638, KB, MCF-7 were evaluated with an SRB assay and the $IC_{50}$ values of cancer cell growth inhibition are summarized in Table 2. 5'-Bromo-5-nitro-indirubin-3'-oxime (2) and Roscovitin were tested together as a positive control in the assay.

TABLE 2

Anti-proliferative activities of 5',5-substitutied indirubin-3'-oxime derivatives on different human cancer cell lines

| Compound | $R_1$ | $R_2$ | A549[b] | HT1080[c] | HCT116[d] | K562[e] | SNU638[f] | KB[g] | MCF-7[h] |
|---|---|---|---|---|---|---|---|---|---|
| 11a | OH | Cl | 16.4 | 2.92 | 3.5 | 12.2 | 5.14 | 10.2 | 10.7 |
| 11b | OH | $NO_2$ | 3.33 | 0.45 | 0.44 | 0.91 | 1.03 | 1.3 | 1.2 |
| 11c | OH | F | 4.09 | 0.68 | 1.66 | 1.4 | 2.11 | 4.6 | 2.6 |
| 11d | OH | $OCF_3$ | 16.9 | 2.28 | 2.25 | 5.9 | 2.96 | 5.8 | 4.2 |

$IC_{50}$ (μM)

TABLE 2-continued

Anti-proliferative activities of 5',5-substitutied indirubin-3'-oxime
derivatives on different human cancer cell lines

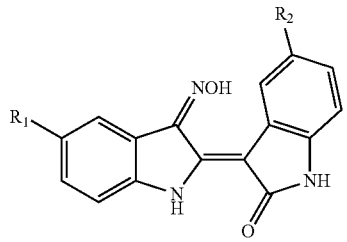

| Compound | $R_1$ | $R_2$ | A549[b] | HT1080[c] | HCT116[d] | K562[e] | SNU638[f] | KB[g] | MCF-7[h] |
|---|---|---|---|---|---|---|---|---|---|
| | | | | | IC$_{50}$ (μM) | | | | |
| 12a | Cl | Cl | >20 | 12.2 | 1.86 | 17.2 | 2.57 | 11.9 | 6.1 |
| 12b | Cl | NO$_2$ | 15.6 | 1.25 | 0.33 | 0.56 | 1.16 | 1.1 | 0.5 |
| 12c | Cl | F | 18.9 | 3.62 | 1.7 | 14.7 | 2.28 | 3.6 | 3.5 |
| 12d | Cl | OCF$_3$ | >20 | 17.7 | 3.79 | >20 | 2.71 | 2.8 | 4.2 |
| 13a | F | Cl | >20 | 5.33 | 3.3 | 7.14 | 6.32 | 9.1 | 7 |
| 13b | F | NO$_2$ | 0.57 | 0.64 | 0.28 | 0.46 | 0.94 | 0.9 | 0.9 |
| 13c | F | F | 10.3 | 8.6 | 13.5 | 15.9 | 2.23 | 13.2 | 6.57 |
| 13d | F | OCF$_3$ | 19.9 | 3.95 | 1.5 | 1.5 | 1.89 | 3.8 | 4.1 |
| 14a | CH$_3$ | Cl | >20 | >20 | 18.8 | >20 | 12.7 | 5.18 | 8.79 |
| 14b | CH$_3$ | NO$_2$ | >20 | 3.92 | 1.41 | 0.8 | 1.06 | 2.1 | 1.06 |
| 14c | CH$_3$ | F | >20 | >20 | >20 | >20 | 11.5 | 10.6 | 10.5 |
| 14d | CH$_3$ | OCF$_3$ | >20 | >20 | >20 | >20 | >20 | 8.13 | 7.3 |
| 16a | OCH$_3$ | NO$_2$ | >20 | >20 | >20 | >20 | >20 | >20 | >20 |
| 16h | OCH$_3$ | F | 6.71 | 4.84 | 3.59 | 5.29 | 13.6 | >20 | >20 |
| 16e | OCH$_3$ | OCF$_3$ | >20 | >20 | >20 | >20 | >20 | 20 | 13 |
| 2[i] | Br | NO$_2$ | 16.9 | 1.45 | 0.45 | 0.77 | 1.14 | 1.16 | 0.95 |
| Roscovitin[i] | | | | 14.7 | 16.8 | 17.8 | >20 | 9.77 | 30.1 | 14.7 |

[a] A series of indirubin derivatives were tested at five concentrations for their effects on various human cancer cell lines using SRB assay, as described in the Experimental Section. The IC$_{50}$ (μM) values were calculated from dose response curves. [b] human lung cancer cell. [c] human fibro sarcoma cell. [d] human colon cancer cell. [e] human leukemia cell. [f] human stomach cancer cell. [g] human nasopharyngeal cancer cell. [h] human breast cancer cell. [i] Experiments was also performed with 2 and Roscovitin as positive control.

The anti-proliferative activities of 5'-hydroxy derivatives, 11a-d is well correlated with the potency of their inhibitory activities against CDK2 depending on the substituents at the 5 position with following order NO$_2$>F>Cl, OCF$_3$. Particularly, 5'-hydroxy-5-nitro-indirubin-3'-oxime, 11b displayed similar or improved inhibitory activity depending on the cancer cells, compared with 2, with IC$_{50}$ values of ~0.4 μM against HT1080 and HCT116 cell line. Among the compounds with replacement of 5'-bromo group of 2 by other halogen groups such as F and Cl, 5-nitro analogs, 12b and 13b showed more effective than 5'-bromo-5-nitro-indirubin-3'-oxime compound 2, especially, against the proliferation of human colon cancer cells, HCT116, which has deregulated cyclinD1, with IC$_{50}$ values of approximately 0.3 μM.

Particularly, 5'-fluoro-5-nitiro-indirubin-3'-oxime, 13b showed the most broad spectrum of inhibitory potency against all of the cancer cells (IC$_{50}$=0.28~0.94 μM) with the correlation of its potent inhibitory activity of CDK2. Compound 13b has an exclusive anti-proliferative activity with a nanomolar IC50 value against human lung cancer cells, A549 in contrast to the weak activities of most of other derivatives. However, indirubin-3'-oxime derivatives substituted with electron donating groups such as 5'-CH$_3$, 5'-OCH$_3$, 14 and 16 were very weak inhibitors against majority of the cancer cells, except for 5'-methyl-5-nitro-3'-oxime, 14b, of which anti-proliferative activities were in the range of 0.8~1 μM of IC$_{50}$ values. Regarding the effect of substitutions at 5-position ($R_2$), 5-NO$_2$ group in combination with 5'-OH, Cl, F, CH$_3$ showed the most potent anti-proliferative effect among the series of 5',5-disubstituted derivatives. This result is in good agreement with our previously published results[23] and supported by the hypothesized binding mode of 2 and 11b, in which additional binding with a salt bridge might be formed between 5-nitro group and Asp 145, Lys33 in the ATP binding site of CDK2. In the case of 5'-OCH$_3$ derivatives, only 5-F substituted analog, 16b displayed moderate anti-proliferative activity, indicating different mechanism of action might be associated for this analog. The combined results in this study suggest an important insight that the 5'-hydroxyl or halogen groups could be favorable either to inhibit CDK and cancer cell growth possibly by forming additional hydrogen bonding interaction at the ATP binding site of CDK2.

In-vivo Anti-Cancer Activity of 11b

Figure 5:
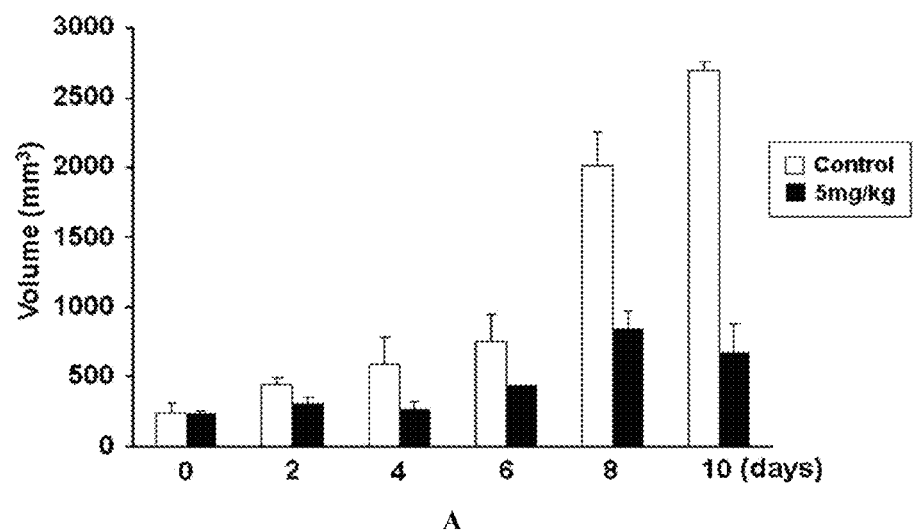
FIG. 5 shows an inhibition of xenografted tumor growth by 11b.
Figure 5:
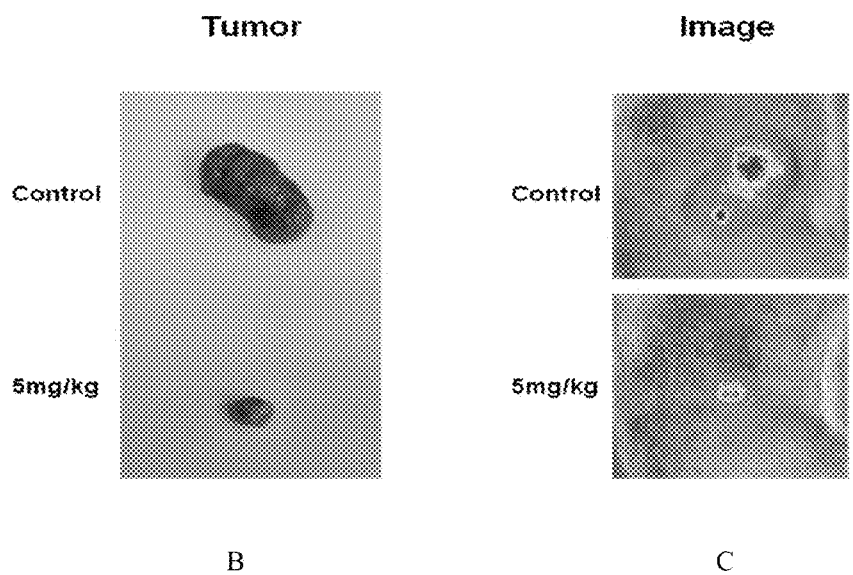

To explore the effects of 5'-OH-5-nitro analog, 11b in vivo, a tumor xenograft animal model of Sprague Dawley (SD) rats, in which RK3E rat kidney cells harboring the k-ras and GFP/Luc gene were subcutaneously transplanted, was utilized as published by our group. Five days after the transplantation, 5 mg/kg of 11b was administered i.v. to the animal every other day for a total of five times with daily monitoring. The tumor volume was significantly decreased by about 84.3% compared with control groups (FIG. 5(a) and FIG. 5(b)). There was no significant difference in body weight during the administration of 11b compared with control group (data not shown). Bioluminescence image obtained on day 10 after the treatment of 11b indicated that the luminescence intensity, an indicator of tumor growth, was significantly decreased (FIG. 5(c)).

Figure 6:
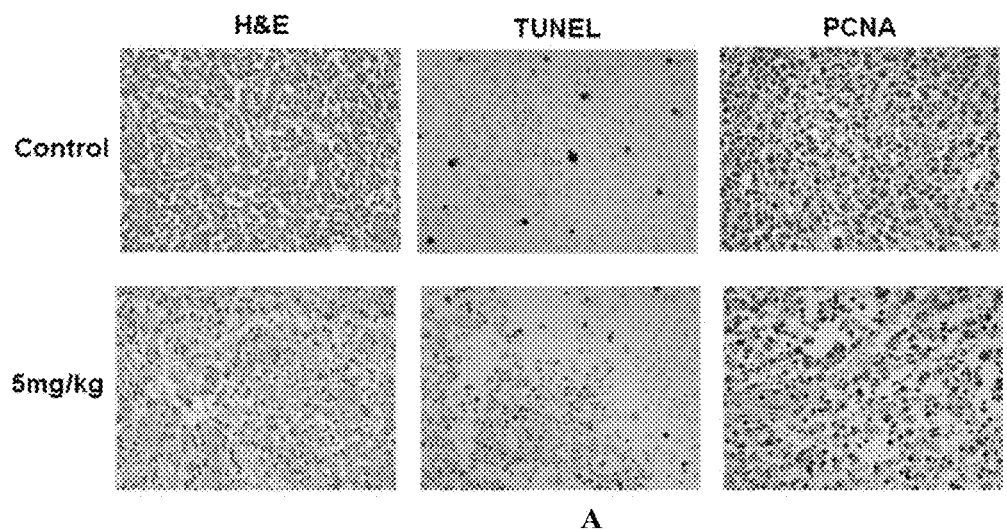
FIG. 6 shows a histology and immunohistochemistry of tumor tissue. RK3E-ras-Luc cells were inoculated s.c. on the left flank of rats. 11b (5 mg/kg) was injected intravenously into the tumor bearing rats every other day beginning from day 5. The rats were sacrificed on day 11.
Figure 6:
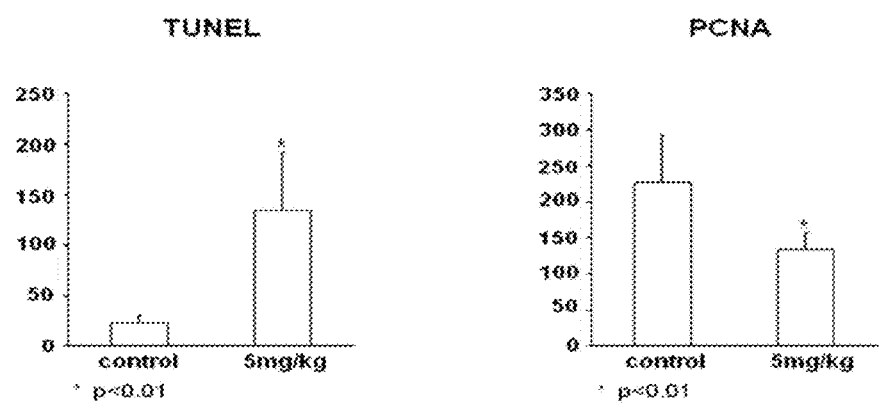

Histological analysis showed that the untreated control solid tumor belonged to anaplastic undifferentiated carcinoma showing many mitotic figures, multifocal necrosis, and hemorrhage. However, 11b treated tumor led to extensive cell death (FIG. 6(a), left). TUNEL-positive apoptotic cells were increased about 6.0 fold tissue from 11b treated animals compared with control tissue (FIG. 6(a) middle, and FIG. 6(b)). On the other hand, the expression level of PCNA, a cell proliferation marker, was decreased in 11b treated animals as compared with control (FIG. 6(a) right, and FIG. 6(c)). These results indicate that 11b suppresses tumor growth through inhibition of cell proliferation and activating apoptosis in vivo.

In summary, several novel 5',5-substituted-indirubin-3'-oxime compounds were developed as potent inhibitors against CDK1 and 2 with anti-proliferative activities in various cancer cell lines. The enhanced inhibitory activities of 5',5-substituted indirubin-3'-oxime derivatives, compared to 5'-unsubstituted indirubin-3'-oxime, 1 could be interpreted with a molecular docking study at the ATP binding site of CDK2 resulting in the determination of additional projection of the molecule toward solvent accessible region and interactions with presented amino acid residues of ATP binding pocket exemplified with 5'-hydroxy analog, 11b. Especially, 5'-hydroxy-5-nitro-indirubin-3'-oxime (11b) and 5'-fluoro-5-nitro-indirubin-3'-oxime (13b) were potent CDK2 inhibitors with $IC_{50}$ values of 1.71 nM and 1.91 nM, respectively, as well as potent anti-proliferative agents for several human cancer cell lines with IC50 values in the range of 0.2~3.3 µM. Structure-activity relationship analysis showed that OH and halogen groups were preferred to the electron donating groups such as 5'-$CH_3$, 5'-$OCH_3$ at 5' position. A representative analog, 5'-hydroxy-5-nitro-indirubin-3'-oxime (11b) displayed more than 500-fold selectivity of the inhibitory activity against CDK over selected kinase panel and significant in-vivo anti-cancer activities as well. The information resulted from this study could be expected to contribute to the development of CDK inhibitor based drug design and clinical applications.

Further, other analogs, such as, 5'-hydroxy-5-chloro-indirubin-3'-oxime (11a), 5'-hydroxy-5-fluoro-indirubin-3'-oxime (11c), 5'-chloro-5-nitro-indirubin-3'-oxime (12b) and 5'-methyl-5-nitro-indirubin-3'-oxime (14b) can be considered as effective anti-cancer agent.

The present invention can be explained more concretely by following examples. However, the scope of present invention shall not be interpreted by limiting following examples.

EXAMPLES

Chemistry $^1$H NMR spectra were determined with a JEOL JNM-LA 300WB spectrometer at 300 MHz or JEOL JNM-ECX 400P spectrometer at 400 MHz, and spectra were taken in $CDCl_3$ or DMSO-$d_6$ or Acetone-$d_6$. Unless otherwise noted, chemical shifts are expressed as ppm downfield from internal tetramethylsilane, or relative ppm from DMSO (2.5 ppm), Acetone (2.04 ppm). Mass spectroscopy was carried out on electrospray and high-resolution mass spectra (m/z) were recorded on a FAB, EI [JEOL: mass range 2600 amu, 10 kV acceleration)] and ESI. High-resolution mass analysis was performed at Korea Basic Science Institute (Daegu).

The purity of all final products was determined by HPLC (at least 95% purity unless otherwise noted). The determination of purity was performed on a Shimadzu SCL-10A VP HPLC system using a Shimadzu Shim-pack C18 analytical column (250 mm 4.6 mm, 5 m, 100 Å in linear gradient solvent systems. Solvent system was $H_2O:CH_3CN$=65:35 to 5:95 over 30 min at a flow rate=1 mL/min. Peaks were detected by UV absorption using a diode array detector.

Example 1

Preparation of 5-substituted indoxyl N,O-diacetate 5a-d

To a solution of 5-substituted anthranilic acid (1.0 g, 6.45 mmol) in 50 ml of methanol was added 0.5 ml of acetic acid, followed by ethyl glyoxalate (1 ml, 9.7 mmol) and $NaCNBH_3$ (609.5 mg, 9.7 mmol). The reaction mixture was stirred for 3 h at room temperature. Then the methanol was removed by evaporation. The residue was taken up in solution of saturated $NH_4Cl$ in water and extracted with ethyl acetate. The combined extracts were dried over sodium sulfate, filtered and evaporated. The product was purified by silica gel column chromatography ($CH_3Cl$:methanol=30:1) and then these product (1.4 g, 5.8 mmol) was hydrolyzed in 25 ml of 1 N NaOH(aq) and 10 ml of methanol. The reaction mixture was stirred for 1 h at room temperature and the resulting solution was acidified by 1N HCl. The precipitate formed was collected by filtration and washed with water. Obtained di-acid compounds, 4a-d (1.2 g, 4.97 mmol) was added in acetic anhydride (15 ml) and $Na_2CO_3$ (1.3 g, 12.4 mmol). The reaction mixture was refluxed for 4 h. The product was extracted with ethyl acetate and washed with water. The combined extracts were dried over sodium sulfate, filtered and evaporated. The product was purified by silica gel column chromatography (Hexane:Ethyl acetate=2:1).

Data for 1-Acetyl-1 H-indole-3,5-diyl diacetate (5a)
$^1$H NMR ($CDCl_3$, 300 MHz, ppm, J in Hz) 8.46 (1H, d, J=9.3 Hz), 7.76 (1H, s), 7.30 (1H, d, J=2.4 Hz), 7.11 (1H, dd, J=9.3, 2.4 Hz), 2.67 (3H, s), 2.36 (3H, s), 2.31 (3H, s). ESI [M-H]$^-$: 273.83.

Data for 1-Acetyl-5-chloro-1 H-indol-3-yl acetate (5b)
$^1$H NMR ($CDCl_3$, 400 MHz, ppm, J in Hz) 8.40 (1H, d, J=8.8 Hz), 7.75 (1H, s), 7.53 (1H, d, J=2 Hz), 7.34 (1H, dd, J=8.8, 2 Hz), 2.61 (3H, s), 2.39 (3H, s). ESI [M-H]$^-$: 249.83.

Data for 1-Acetyl-5-fluoro-1 H-indol-3-yl acetate (5c)
$^1$H NMR ($CDCl_3$, 400 MHz, ppm, J in Hz) 8.42 (1H, m), 7.75 (1H, s), 7.19 (1H, dd, J=8.2, 2.4 Hz), 7.10 (1H, td, J=8.8, 2.4 Hz), 2.59 (3H, s), 2.37 (3H, s). ESI [M-H]$^-$: 233.88.

Data for 1-Acetyl-5-methyl-1 H-indol-3-yl acetate (5d)
$^1$H NMR ($CDCl_3$, 400 MHz, ppm, J in Hz) 8.31 (1H, d, J=7.6 Hz), 7.65 (1H, s), 7.31 (1H, s), 7.19 (1H, d, J=7.6 Hz), 2.57 (3H, s), 2.44 (3H, s), 2.36 (3H, s). ESI [M-H]$^-$: 229.80.

Example 2

Preparation of 5',5-substituted indirubin-3'-oxime derivatives 11-14

To a solution of isatin analogs (77 mg, 0.425 mmol) in methanol (5 ml) were added 5-substituted indoxy N, O diacetate (100 mg, 0.425 mmol) and the mixture was stirred for 5 min. Anhydrous $Na_2CO_3$ (112.5 mg, 1.06 mmol) was added, and the stirring was continued for 3 h at room temperature. The dark precipitate was filtered and washed with cold water, and dried under reduced pressure to give derivatives of 5,5-substituted indirubin, 7-10. The appropriate indirubin derivative (10 mg, 0.032 mmol) was dissolved in pyridine (0.3 ml) and added hydroxylamine hydrochloride (6.6 mg, 0.095 mmol). The reaction mixture was heated under reflux at 120° C. for 2 h. After cooling, the product was acidified with 1N HCl. The precipitation was filtered and washed with water to afford quantitatively the corresponding 3'-oxime selectively in a (2'Z, 3'E) form. The product was purified by silica gel column chromatography (Chloroform:Methanol=20:1).

Data for (2'Z, 3'E)-5'-Hydroxy-5-chloro-indirubin-3'-oxime (11a)

$^1$H NMR (DMSO, 400 MHz, ppm, J in Hz) 11.71 (1H, s, N—H), 10.78 (1H, s, N'—H), 9.27 (1H, s, O—H), 8.59 (1H, d, J=2 Hz, H-4), 7.74 (1H, d, J=2 Hz, H-4'), 7.24 (1H, d, J=8.4 Hz, H-7), 7.11 (1H, dd, J=8, 2 Hz, H-6'), 6.87 (1H, d, J=8.4 Hz, H-6), 6.85 (1H, d, J=8 Hz, H-7'). HRMS (EI) [M]$^+$ ($C_{16}H_{10}ClN_3O_3$): calcd 327.0411 found 327.0408. Purity 92%.

Data for (2'Z, 3'E)-5'-Hydroxy-5-nitro-indirubin-3'-oxime (11b)

$^1$H NMR (DMSO, 300 MHz, ppm, J in Hz) 13.87 (1H, s, NOH), 11.78 (1H, s, N—H), 11.35 (1H, s, N'—H), 9.41 (1H, d, J=2.8 Hz, H-4), 9.32 (1H, s, O—H), 8.05 (1H, dd, J=11.6, 2.8 Hz, H-6), 7.76 (1H, d, J=3.2 Hz, H-4'), 7.29 (1H, d, J=11.6 Hz, H-7), 7.04 (1H, d, J=11.2 Hz, H-7'), 6.86 (1H, dd, J=11.2, 3.2 Hz, H-6'). HRMS (EI) [M]$^+$($C_{16}H_{10}N_4O_5$): calcd 338.0651 found 338.0648.

Data for (2'Z, 3'E)-5'-Hydroxy-5-fluoro-indirubin-3'-oxime (11c)

$^1$H NMR (DMSO, 400 MHz, ppm, J in Hz) 11.69 (1H, s, N—H), 10.66 (1H, s, N'—H), 9.25 (1H, s, O—H), 8.42 (1H, dd, J=11.4, 2.8 Hz, H-6), 7.73 (1H, d, J=2.4 Hz, H-4'), 7.24 (1H, d, J=8.4 Hz, H-6'), 6.81-6.99 (3H, m, H-7', H-4, H-7). HRMS (EI) [M]$^+$($C_{16}H_{10}FN_3O_3$): calcd 311.0706 found 311.0707. Purity 93%.

Data for (2'Z, 3'E)-5'-Hydroxy-5-trifluoromethoxy-indirubin-3'-oxime (11d)

$^1$H NMR (DMSO, 400 MHz, ppm, J in Hz) 11.70 (1H, s, N—H), 10.78 (1H, s, N'—H), 9.22 (1H, s, O—H), 8.50 (1H, s, H-4), 7.70 (1H, d, J=2 Hz, H-4'), 7.21 (1H, d, J=8.8 Hz, H-7'), 7.03 (1H, d, J=8.4 Hz, H-7), 6.88 (1H, d, J=8.4 Hz, H-6), 6.80 (1H, dd, J=8.8, 2.4 Hz, H-6'). HRMS (ESI) [M-H]$^-$ ($C_{17}H_9F_3N_3O_4$): calcd 376.0545 found 376.0546.

Data for (2'Z, 3'E)-5'-Chloro-5-chloro-indirubin-3'-oxime (12a)

$^1$H NMR (acetone, 300 MHz, ppm, J in Hz) 13.05 (1H, s, NOH), 11.82 (1H, s, N—H), 9.81 (1H, s, N'—H), 8.67 (1H, s, H-4), 8.35 (1H, d, J=1.8 Hz, H-4'), 7.45 (2H, m, H-6, H-7), 7.16 (1H, d, J=8.4 Hz, H-6'), 6.97 (1H, d, J=8.4 Hz, H-7'). HRMS (EI) [M]$^+$($C_{16}H_9Cl_2N_3O_2$): calcd 345.0072 found 345.0075.

Data for (2'Z, 3'E)-5'-Chloro-5-nitro-indirubin-3'-oxime (12b)

$^1$H NMR (DMSO, 400 MHz, ppm, J in Hz) 11.98 (1H, s, N—H), 11.39 (1H, s, N'—H), 9.45 (1H, s, H-4), 8.25 (1H, s, H-4'), 8.08 (1H, d, J=7.6 Hz, H-6), 7.50 (2H, m, H-6', H-7), 7.05 (1H, d, J=8.4 Hz, H-7'). HRMS (ESI) [M-H]$^-$ ($C_{16}H_8ClN_4O_4$): calcd 355.0234 found 355.0242.

Data for (2'Z, 3'E)-5'-Chloro-5-fluoro-indirubin-3'-oxime (12c)

$^1$H NMR (acetone, 300 MHz, ppm, J in Hz) 12.96 (1H, s, NOH), 11.78 (1H, s, N—H), 9.71 (1H, s, N'—H), 8.41 (1H, d, J=11.4 Hz, H-7), 8.32 (1H, s, H-4), 7.40-7.50 (2H, m, H-4', H-6'), 6.88-6.91 (2H, m, H-6, H-7'). HRMS (ESI) [M-H]$^-$ ($C_{16}H_8ClFN_3O_2$): calcd 328.0289 found 328.0291.

Data for (2'Z, 3'E)-5'-Chloro-5-trifluoromethoxy-indirubin-3'-oxime (12d)

$^1$H NMR (acetone, 300 MHz, ppm, J in Hz) 13.02 (1H, s, NOH), 11.82 (1H, s, N—H), 9.88 (1H, s, N'—H), 8.63 (1H, s, H-4), 8.34 (1H, d, J=2.1 Hz, H-4'), 7.47 (2H, m, H-6, H-7), 7.11 (1H, d, J=8.4 Hz, H-6'), 7.03 (1H, d, J=8.4 Hz, H-7'). HRMS (ESI) [M-H]$^-$ ($C_{17}H_8ClF_3N_3O_3$): calcd 394.0206 found 394.0215.

Data for (2'Z, 3'E)-5'-Fluoro-5-chloro-indirubin-3'-oxime (13a)

$^1$H NMR (DMSO, 400 MHz, ppm, J in Hz) 11.81 (1H, s, N—H), 10.85 (1H, s, N'—H), 8.62 (1H, d, J=2.4 Hz, H-4), 7.97 (1H, dd, J=8.2, 2.4 Hz, H-6), 7.47 (1H, m, H-4'), 7.31 (1H, m, H-7), 7.15 (1H, dd, J=8.4, 2 Hz, H-6'), 6.88 (1H, d, J=8.4 Hz, H-7'). HRMS (ESI) [M-H]$^-$ ($C_{16}H_8ClFN_3O_2$): calcd 328.0289 found 328.0295.

Data for (2'Z, 3'E)-5'-Fluoro-5-nitro-indirubin-3'-oxime (13b)

$^1$H NMR (DMSO, 400 MHz, ppm, J in Hz) 11.89 (1H, s, N—H), 11.40 (1H, s, N'—H), 9.43 (1H, d, J=2 Hz, H-4), 8.08 (1H, dd, J=8.6, 2 Hz, H-6), 8.00 (1H, dd, J=8.6, 2 Hz, H-7), 7.51 (1H, m, H-4'), 7.33 (1H, td, J=9, 2.8 Hz, H-6'), 7.06 (1H, d, J=8.4 Hz, H-7'). HRMS (EI) [M]$^+$($C_{16}H_9FN_4O_4$): calcd 340.0608 found 340.0610.

Data for (2'Z, 3'E)-5'-Fluoro-5-fluoro-indirubin-3'-oxime (13c)

$^1$H NMR (DMSO, 400 MHz, ppm, J in Hz) 11.76 (1H, s, N—H), 10.68 (1H, s, N'—H), 8.41 (1H, dd, J=11.2, 2.4 Hz, H-4), 7.93 (1H, dd, J=8.8, 2.4 Hz, H-4'), 7.39 (1H, m, H-7), 7.30 (1H, td, J=8.8, 2 Hz, H-6), 6.93 (1H, td, J=9, 2.4 Hz, H-6'), 6.84 (1H, m, H-7'). HRMS (EI) [M]$^+$($C_{16}H_9F_2N_3O_2$): calcd 313.0663 found 313.0666. Purity 93%.

Data for (2'Z, 3'E)-5'-Fluoro-5-trifluoromethoxy-indirubin-3'-oxime (13d)

$^1$H NMR (DMSO, 400 MHz, ppm, J in Hz) 12.02 (1H, s, N—H), 10.72 (1H, s, N'—H), 8.59 (1H, s, H-4), 8.02 (1H, dd, J=8.8, 2.4 Hz, H-6), 7.41 (1H, m, H-4'), 7.18 (1H, td, J=9.2, 2 Hz, H-6'), 7.00 (1H, d, J=8.4 Hz, H-7), 6.9 (1H, d, J=8.4 Hz, H-7'). HRMS (FAB) ($C_{17}H_9O_3N_3F_4$): calcd 379.0579 found 379.0580.

Data for (2'Z, 3'E)-5'-Methyl-5-chloro-indirubin-3'-oxime (14a)

$^1$H NMR (DMSO, 400 MHz, ppm, J in Hz) 11.85 (1H, s, N—H), 10.76 (1H, s, N'—H), 8.64 (1H, s, H-4), 8.10 (1H, s, H-4'), 7.29 (1H, d, J=8.4 Hz, H-6), 7.20 (1H, d, J=8.4 Hz, H-7), 7.10 (1H, d, J=8.2 Hz, H-6'), 6.86 (1H, d, J=8.4 Hz, H-7'), 2.31 (3H, s, CH$_3$). HRMS (EI) [M]$^+$($C_{17}H_{12}ClN_3O_2$): calcd 325.0618 found 325.0623.

Data for (2'Z, 3'E)-5'-Methyl-5-nitro-indirubin-3'-oxime (14b)

$^1$H NMR (DMSO, 400 MHz, ppm, J in Hz) 11.87 (1H, s, N—H), 11.38 (1H, s, N'—H), 9.46 (1H, d, J=2.4 Hz, H-4), 8.11 (1H, s, H-4'), 8.07 (1H, dd, J=8, 2.4 Hz, H-6), 7.37 (1H, d, J=8 Hz, H-7), 7.26 (1H, d, J=8.8 Hz, H-6'), 7.05 (1H, d, J=8.8 Hz, H-7'), 2.32 (3H, s, CH$_3$). HRMS (ESI) [M-H]$^-$ ($C_{17}H_{11}N_4O_4$): calcd 335.0780 found 335.0787. Purity 93%.

Data for (2'Z, 3'E)-5'-Methyl-5-fluoro-indirubin-3'-oxime (14c)

$^1$H NMR (DMSO, 400 MHz, ppm, J in Hz) 11.78 (1H, s, N—H), 10.61 (1H, s, N'—H), 8.43 (1H, dd, J=11.2, 2.4 Hz, H-4), 8.06 (1H, s, H-4'), 7.26 (1H, d, J=8.4 Hz, H-7), 7.17 (1H, d, J=8 Hz, H-7'), 6.86 (1H, td, J=8.4, 2.4 Hz, H-6), 6.80 (1H, d, J=8 Hz, H-6'), 2.28 (3H, s, CH$_3$). HRMS (EI) [M]$^+$ ($C_{17}H_{12}FN_3O_2$): calcd 309.0914 found 309.0912.

Data for (2'Z, 3'E)-5'-Methyl-5-trifluoromethoxy-indirubin-3'-oxime (14d)

$^1$H NMR (DMSO, 400 MHz, ppm, J in Hz) 11.80 (1H, s, N—H), 10.87 (1H, s, N'—H), 8.59 (1H, d, J=2 Hz, H-4), 8.09 (1H, s, H-4'), 7.34 (1H, d, J=8.4 Hz, H-6), 7.25 (1H, d, J=8 Hz, H-7), 7.10 (1H, d, J=7.4 Hz, H-6'), 6.94 (1H, d, J=8.4 Hz, H-7'), 2.33 (3H, s, CH$_3$). HRMS (EI) [M]$^+$($C_{18}H_{12}F_3N_3O_3$): calcd 375.0831 found 375.0833.

Example 3

Preparation of 5'-methoxy-5-substituted indirubin-3'-oxime derivatives 16a-c

To a solution of 5'-hydroxy-indirubin analogs, 7d (10 mg, 0.028 mmol) in acetone (1 ml) were dropped methyl iodide (17 L, 0.276 mmol) and added $K_2CO_3$ (19 mg, 0.138 mmol) and the stirring was continued for 4 h at room temperature. The dark precipitate was filtered and washed with cold water, and dried under reduced pressure to give derivatives of 5'-methoxy-5-substituted indirubin, 15c. The appropriate indirubin derivative (6 mg, 0.016 mmol) was dissolved in pyridine (0.3 ml) and added hydroxylamine hydrochloride (3.4 mg, 0.048 mmol). The reaction mixture was heated under reflux at 120° C. for 1 h. After cooling, the product was acidified with 1N HCl. The precipitation was filtered and washed with water to afford quantitatively the corresponding 3'-oxime selectively in a (2'Z, 3'E) form. The product was purified by silica gel column chromatography (Hexane:Ethyl acetate=2:1).

Data for (2'Z, 3'E)-5'-Methoxy-5-nitro-indirubin-3'-oxime (16a)

$^1$H NMR (DMSO, 400 MHz, ppm, J in Hz) 11.82 (1H, s, N—H), 9.46 (1H, d, J=2.4 Hz, H-4), 9.33 (1H, s, N'—H), 8.12 (1H, dd, J=8.4, 2.4 Hz, H-6), 7.77 (1H, d, J=2.4 Hz, H-4'), 7.30 (1H, d, J=8.4 Hz, H-7), 7.24 (1H, d, J=9.2 Hz, H-7'), 6.85 (1H, dd, J=7.8, 2.4 Hz, H-6'), 3.39 (3H, s, $OCH_3$). HRMS (ESI) [M-H]$^-$ ($C_{17}H_{11}N_4O_5$): calcd 351.0729 found 351.0724. Purity 94%.

Data for (2'Z, 3'E)-5'-Methoxy-5-fluoro-indirubin-3'-oxime (16b)

$^1$H NMR (DMSO, 400 MHz, ppm, J in Hz) 11.68 (1H, s, N—H), 9.22 (1H, s, N'—H), 8.44 (1H, m, H-4), 7.70 (1H, d, J=2.4 Hz, H-4'), 7.21 (1H, d, J=8.8 Hz, H-6), 6.96 (2H, m, H-7, H-7'), 6.79 (1H, dd, J=8.6, 2.4 Hz, H-6'), 3.26 (3H, s, $OCH_3$). HRMS (EI) [M]$^+$($C_{17}H_{12}FN_3O_3$): calcd 325.0863 found 325.0859.

Data for (2'Z, 3'E)-5'-Methoxy-5-trifluoromethoxy-indirubin-3'-oxime (16c)

$^1$H NMR (acetone, 400 MHz, ppm, J in Hz) 11.70 (1H, s, N—H), 8.62 (1H, s, H-4), 8.28 (1H, s, N'—H), 7.90 (1H, d, J=2.4 Hz, H-4'), 7.24 (1H, d, J=8.4 Hz, H-6), 7.12 (1H, m, H-7'), 7.04 (1H, d, J=8.4 Hz, H-7), 6.99 (1H, dd, J=8.4, 2.4 Hz, H-6'), 3.33 (3H, s, $OCH_3$). HRMS (EI) [M]$^+$ ($C_{18}H_{12}F_3N_3O_4$): calcd 391.0780 found 391.0782.

Example 4

Molecular Docking

Molecular docking was performed using CDocker, a CHARMm-based molecular dynamics docking algorithm on Discovery Studio 2.0 (Accelrys). The CDK2 structure co-crystallized with 5-bromo-indirubin was obtained from the PDB data bank (PDB code: 2BHE). A protein clean process and a CHARMm-force field were sequentially applied. The area around 5-bromo-indirubin was chosen as the active site, with the radius set as at 8 Å. After removing the ligand from the structure of the complex, a binding sphere in the three axis directions was constructed around the active site. All default parameters were used in the docking process. CHARMm-based molecular dynamics (1,000 steps) were used to generate random ligand 11b conformations and the position of any ligand 11b was optimized in the binding site using rigid body rotation followed by simulated annealing at 700K. Final energy minimization was set as the full potential mode. The final binding conformation of 11b was determined on the basis of energy. Docking study of ligand 2, 13b was carried out as described above.

Example 5

Biological Methods

Enzyme Assay.

CDK1/cyclin B, CDK2/cyclin E were purchased from Milipore (Billerica, Mass.). The kinase activity was tested in buffer (8 mM MOPS pH 7.0, 0.2 mM EDTA, 10 mM MgAcetate), with 0.1 mg/mL histone H1, in the presence of 45 M [—$^{33}$P] ATP (500 cpm/pmol) for CDK1 or 120 µM [γ—$^{33}$P] ATP (500 cpm/pmol) for CDK2 in a final reaction volume of 25 µM. The reaction was initiated by the addition of the MgATP mix. After incubation for 40 min at 30° C., the reaction was stopped by the addition of 5 µL of 3% phosphoric acid solution. 10 µL aliquots of supernatant were spotted onto 2.5 cm×3 cm pieces of Whatman P30 phosphocellulose paper, and 20 s later, the filters were washed three times for 5 min in 75 mM phosphoric acid and once in methanol prior to drying. The wet filters were counted in the presence of 1 mL of ACS (Amersham) scintillation fluid. The activities are usually expressed as a percentage of the maximal activity, i.e., in the absence of inhibitors. Controls were applied with appropriate dilutions of DMSO.

Inhibition of kinase activity against a variety of recombinant kinases (c-Met, Met M1250T, Ron, VEGF2, EGFR, TrkA, PI3Kγ, IKKβ Insulin receptor, Aurora A) was measured using homogeneous time-resolved fluorescence (HTRF) assays. Briefly, assays are based on the phosphorylation of peptide substrates in the presence of ATP. Resulting phosphorylated substrates are detected by TR-FRET (Time Resolved-Fluorescence Resonance Energy Transfer) signal. Recombinant proteins containing kinase domain were purchased from Millipore (Billerica, Mass.). Optimal enzyme, ATP, and substrate concentrations were established for each enzyme using HTRF KinEASE kit (Cisbio) according to the manufacturer's instruction. Assays are consisted of enzymes mixed with serially diluted compounds and peptide substrates in kinase reaction buffer (250 mM HEPES (pH 7.0), 0.5 mM orthovanadate, 0.05% BSA, 0.1% $NaN_3$). Following the addition of reagents for detection, TR-FRET signal was measured using EnVision multi-label reader (Perkin Elmer, Waltham, Mass.).

Cell Proliferation Assay.

Cells (A549, HT1080, HCT116, K562, SNU638, KB, MCF-7) were counted, diluted to $5\times10^4$ cells/mL with fresh medium (MEME, DMEM or RPMI containing 10% FBS), and added 190 µL of cell suspension to 96-well plates containing various concentrations of test compounds (10 µL in 10% aqueous DMSO). Test plates were incubated for 3 days at 37° C. in $CO_2$ incubator. For zero day controls, cells were incubated for 30 min at 37° C. in $CO_2$ incubator. All treatments were performed in triplicate. After the incubation periods, cells were fixed with 50 µL of cold 50% TCA at 4° C. for 30 min, washed 5 times with tap water, and air-dried. The fixed cells were stained with 0.4% SRB solution in 1% aqueous acetic acid at room temperature for 1 h. Free SRB solution was then removed by rinsing 5 times with 1% acetic acid, and air-dried. The bound dye was dissolved with 200 L of 10 mM Tris-base (pH 10.0), and absorbance was determined at 515 nm using an ELISA microplate reader. Finally, the absorbance values obtained with each of the treatment procedures were averaged, and the average values obtained with the zero day control were subtracted. These results were expressed as a percentage, relative to solvent treated control incubations, and $IC_{50}$ values were calculated using non-linear regression analysis (percent survival versus concentration).

Tumor Xenograft Animal Model

The k-ras-transformed rat kidney epithelial cell line (RK3E-ras) were maintained in DMEM supplemented with 10% FCS, 100 units/mL penicillin, and 100 Ag/mL streptomycin. RK3E-ras cells were kindly provided by Dr. Eric Fearon (University of Michigan Medical School, Ann Arbor, Mich.) and have been described in the previous report. Male SD rats (6 weeks of age) were used to examine the inhibition of tumor growth in vivo. RK3E-ras-Luc cells ($5\times10^6$) were implanted subcutaneously into the flank of the rats on Day 0, and rats were grouped randomly (5 mice/group) on Day 5 as previously described. A solution of 11b in a mixture of PEG400, EtOH and DW (30:33:37, 3 mg/mL, 5 mg/kg) were delivered intravenously in a non-anesthesia state every other day for a total of five times. The animals were sacrificed 48 hr after the final administration, and rat weights and tumor volumes were measured. The tumor growth volumes were calculated as follows: $V=(ab^2)/2$, where, a is the longest diameter and b is the shortest diameter of the tumor. All experiments were conducted under protocols approved by the Animal Care and Use Committee at Chosun University School of Dentistry (Gwangju, South Korea).

Bioluminescence Imaging Assay

For bioluminescence imaging, the rats received an i.p. injection of luciferin (Molecular Probes, Palo Alto, Calif.) with Rumpun/ketamine (1:1) anesthesia. The rats were imaged using a LAS-1000 plus imaging System (Fuji film. Tokyo. Japan) to record the bioluminescent signal emitted from the tumor. The LAS-1000 system equipped with a CCD camera was used for acquisition of the emitted light, and Living Image software (Multi Gauge v3.0) was used for data analysis.

Histology, Immunohistochemistry and TUNEL Assay

The excised solid tumors were fixed in 10% buffered formalin and embeddedin paraffin. For optical microscopic examinations, 4-μm sectioned tissues were stained with H&E. Immunohistochemical staining was performed with the avidin-biotin complex method using anti-PCNA antibodies. The immune reactions were visualized with 3,3'-diaminobenzidine and counterstained with Mayer's hematoxylin. A TUNEL assay was performed using an ApopTag PlusPeroxidase In Situ Apoptosis Detection kit (Intergen, Purchase, N.Y.) according to the manufacturer's instructions. Briefly, the slides were deparaffinized and treated with 20 μg/mL proteinase K at 37° C. for 15 min to enhance staining. After immersion 3% hydrogen peroxide to block the endogenous peroxidase, the slides were incubated with a reaction buffer containing terminal de-oxynucleotidyl transferase at 37° C. for 1 h. The slides were then incubated with a peroxidase-conjugated anti-digoxigenin antibody for 30 min, and the reaction products were visualized with a 0.03% 3,3'-diaminobenzidine solution containing 2 mM hydrogen peroxide. The slides were counterstained with 0.5% methyl green.

The invention claimed is:

1. An indirubin-3'-oxime derivative compound as cyclin dependent kinase inhibitor represented by formula (I)

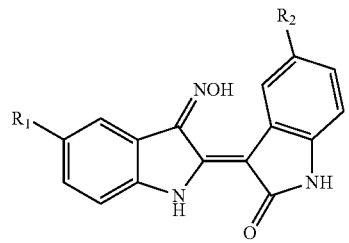

formula (I)

wherein
i) $R_1$ is OH and $R_2$ is $NO_2$;
ii) $R_1$ is F and $R_2$ is $NO_2$;
iii) $R_1$ is OH and $R_2$ is Cl; or
iv) $R_1$ is OH and $R_2$ is F.

* * * * *